United States Patent
Cline

(10) Patent No.: US 10,976,295 B2
(45) Date of Patent: Apr. 13, 2021

(54) SYSTEM AND METHODS FOR METHANE NUMBER GENERATION

(71) Applicant: Mustang Sampling LLC, Ravenswood, WV (US)

(72) Inventor: Richard L. Cline, Missouri City, TX (US)

(73) Assignee: Mustang Sampling LLC, Ravenswood, WV (US)

( * ) Notice: Subject to any disclaimer, the term of this patent is extended or adjusted under 35 U.S.C. 154(b) by 57 days.

(21) Appl. No.: 15/973,877

(22) Filed: May 8, 2018

(65) Prior Publication Data

US 2018/0372709 A1    Dec. 27, 2018

Related U.S. Application Data

(60) Provisional application No. 62/524,836, filed on Jun. 26, 2017.

(51) Int. Cl.
| | |
|---|---|
| *G01N 33/22* | (2006.01) |
| *G01N 33/00* | (2006.01) |
| *G01N 33/28* | (2006.01) |

(52) U.S. Cl.
CPC ....... *G01N 33/225* (2013.01); *G01N 33/0011* (2013.01); *G01N 33/0062* (2013.01); *G01N 33/0073* (2013.01); *G01N 33/2841* (2013.01); *G01N 2033/0068* (2013.01)

(58) Field of Classification Search
CPC ............ G01N 33/225; G01N 33/0062; G01N 33/0068; G01N 33/0073
See application file for complete search history.

(56) References Cited

U.S. PATENT DOCUMENTS

| | | |
|---|---|---|
| 6,429,926 B1 | 8/2002 | Williamson et al. |
| 6,533,065 B2 | 3/2003 | Zanker |
| 6,550,345 B1 | 4/2003 | Letton |
| 7,763,474 B2 | 7/2010 | Hassell |
| 7,895,052 B1 | 2/2011 | Theriot et al. |
| 9,489,484 B2 | 11/2016 | van Dal |
| 10,073,041 B2 | 11/2018 | Pelletier et al. |
| 10,222,302 B1 | 3/2019 | St Amant, III |
| 2006/0288979 A1 | 12/2006 | Ancimer et al. |
| 2008/0288182 A1 | 11/2008 | Cline et al. |
| 2012/0182546 A1* | 7/2012 | Chaouki ............ G01N 21/3563 356/73 |

(Continued)

FOREIGN PATENT DOCUMENTS

| | | |
|---|---|---|
| EP | 3327436 A1 | 5/2018 |
| JP | 2009167411 A | 7/2009 |

(Continued)

OTHER PUBLICATIONS

Appendix D—Methane Number and Fuel Composition. pp. 1-7. Sep. 2011.

(Continued)

*Primary Examiner* — Alexander A Mercado
(74) *Attorney, Agent, or Firm* — Cahn & Samuels, LLP

(57) ABSTRACT

Systems and methods for generating a Methane number for a compressed natural gas fuel by obtaining compositional data from one or more particular analyzers and applying the obtained compositional data to one or more selectable Methane number generation protocols. The systems and methods can include refining of the compressed natural gas fuel to meet a predetermined Methane number.

12 Claims, 8 Drawing Sheets

(56) References Cited

U.S. PATENT DOCUMENTS

| | | | |
|---|---|---|---|
| 2013/0179374 A1 | 7/2013 | Hains et al. | |
| 2015/0377161 A1 | 12/2015 | Smith et al. | |
| 2016/0130516 A1* | 5/2016 | Edlund | C10L 3/106 |
| | | | 48/127.7 |
| 2016/0231296 A1* | 8/2016 | Dressler | G01N 30/8658 |
| 2017/0052092 A1* | 2/2017 | Ascencio | F02C 9/28 |
| 2018/0112622 A1 | 4/2018 | Atterberry et al. | |

FOREIGN PATENT DOCUMENTS

| | | | | |
|---|---|---|---|---|
| KR | 20080057421 A | 6/2008 | | |
| WO | 2010013303 A1 | 2/2010 | | |
| WO | 2016073588 A1 | 5/2016 | | |
| WO | 2017013897 A1 | 1/2017 | | |
| WO | WO2017013897 A1 | 1/2017 | | |
| WO | WO-2018109418 A1 * | 6/2018 | | F02M 21/0215 |
| WO | 2019028178 A1 | 7/2019 | | |

OTHER PUBLICATIONS

Position paper on the impact of including methane number in natural gas regulation. International Group of Liquefied Natural Gas Importers. pp. 1-8. Obtained on Apr. 5, 2017.

Analytically Accurate SVM. Mustang Sampling. pp. 1-2. 2014.

Mustang Intelligent Vaporizer Sampling System SoftView Monitor Software. Mustang Sampling. pp. 1-39. Aug. 2008.

International Search Report, PCT/US18/34408, dated Sep. 14, 2018.

English Abstract of KR20080057421, dated Jun. 25, 2008.

International Search Report and Written Opinion, PCT/US2018/034408, dated Sep. 14, 2018.

Wikipedia, "Custody Transfer," https://en.wikipedia.org/wiki/Custody_transfer, printed on May 13, 2020, pp. 1-10.

Japanese Office Action for Application No. 2019-571225, dated Dec. 10, 2020.

English Language Abstract for WO2017013897.

English Language Abstract for WO2010013303.

* cited by examiner

US 10,976,295 B2

SYSTEM AND METHODS FOR METHANE NUMBER GENERATION

BACKGROUND

Natural gas has been used as a fuel source in vehicles for decades and is becoming increasingly advocated due to social issues such as environmental considerations, diversification of fuel supplies, and high oil prices. Different scales exist to rate the knock resistance of a CNG fuel. Specifically, Methane Number ("MN") and Motor Octane Number ("MON") are both employed as indicators of the "knock tendency" of a combustion engine.

Methane number represents a measure of resistance of fuel gases to engine knock, which is also referred to as detonation. A Methane number is not a thermodynamic property of fuel gas but is a numerical characteristic indicative of combustion control. Engine knock/detonation occurs when a fuel-air mixture auto-ignites ahead of a propagating flame. This phenomenon produces shock waves that could lead to serious loss of power and/or efficiency, as well as damage to the engine.

The knock resistance of a CNG fuel is determined by comparing the compression ratio at which the fuel knocks to that of a reference fuel blend that knocks at the same ratio. Methane numbers are assigned to natural gas supplies based on their operation in a knock testing unit. The reference fuel blend for Methane number includes Methane, which is assigned a value of 100, and hydrogen, which receives a value of 0. For comparison purposes, the primary difference between Methane number and MON is the reference fuel blend that is compared to the natural gas. The fuel blend used as a reference for the MON is comprised of iso-octane, which is assigned an octane number of 100, and n-heptane which receives an octane number of 0. The MON for CNG fuels range from 115 to in excess of 130.

Comparison of fuel characteristics to a particular reference fuel blend, however, is where standard uniformity ends. Specifically, Methane number generation has become increasingly splintered due to use of various formulas and techniques employed to generate the final value, as well as the regulatory environment and particular fuel requirements provided by CNG engine manufacturer protocols applicable to calculations. In particular, it is noted that some gas compositions which do not meet certain quality requirements may still meet compliance of other protocols, particularly if the calculated Methane number is at 80 or above. Under certain circumstances, producers of non-compliant CNG motor fuel can take advantage of these variations in protocols to avoid the more technically difficult and expensive procedure of ethane content reduction, in favor of less difficult and less expensive elimination of heavier hydrocarbons to improve the Methane number.

In general, calculation methods for Methane number are based on experimental measurements of known gases preferably containing only hydrocarbons up to $C_4$. This is because only certain protocols account for higher hydrocarbons, which are often added to the $C_4$ fraction in different ways. Likewise, $H_2$, $CO_2$, and/or $SH_2$ have only been accounted for in some models. In cases where these constituents are not contemplated by a particular calculation method, the effect of their impact is undetermined. Accordingly, variations in calibration gases, differing calculation techniques, and disregard of certain constituents have led to inconsistencies in the value of the final Methane numbers assigned to CNG fuels.

To further complicate matters, no one set of guidelines for Methane number is accepted across various regulatory platforms and by engine manufacturers. Different regulatory entities have issued different standards based on a variety of algorithmic protocols, as have commercial entities associated with custody transfer of LNG. For example, the California Air Resource Board requires compressed natural gas Methane number and Fuel Composition for vehicular use to meet minimal specifications including possessing a Methane number of 80, calculated according to the ASTM D1945 standard. In contrast, in order to maintain warranty coverage, the CNG engine manufacturer Cummins Westport requires a Methane number of 65 or greater for C, B, and L Gas Plus engines and a Methane number of 75 or greater for ISL G and ISX12 G engines, calculated according to Society of Automotive Engineers (SAE) standards.

SUMMARY

A method for receiving data from an analyzing device representative of a compressed natural gas sample analysis and determining a set of established processes for a Methane number generation compatible with the particular analyzing device. The method also includes selecting a first established process from the process set corresponding to a first selected Methane number generation protocol and applying the first established process to the obtained data from the analyzing device to calculate the first Methane number as a function of the selected Methane number generation protocol. The method further includes comparing the first Methane number to a predetermined threshold and refining the compressed natural gas fuel as a function of the comparison.

An exemplary method for initiating a software routine which generates a first field and second field, receiving a selection of an analyzing device via the first field and receiving a selection of the Methane number calculation protocol via the second field. The method further includes calculating a Methane number by applying a measured gas composition value of compressed natural gas fuel received from the selected analyzing device to the selected Methane number calculation protocol and comparing the Methane number to a predetermined threshold. Further, the method includes refining the compressed natural gas fuel as a function of the comparison and generating a transfer ticket including the Methane number.

A system including an analyzing device configured to measure constituents of a compressed natural gas composition and generate data representative thereof, and processing circuitry in communication with said particular analyzing device. The processing circuitry is configured to determine a set of established processes for a Methane number generation compatible with the particular analyzing device, receive a selection of a first established process from the process set corresponding to a first selected Methane number generation protocol, apply the first established process to the obtained data from the analyzer to calculate the Methane number as a function of the selected Methane number generation protocol, compare the Methane number to a predetermined threshold, and control a gas blending control station to refine the compressed natural gas fuel as a function of the comparison.

DETAILED DESCRIPTION

Figure 1:
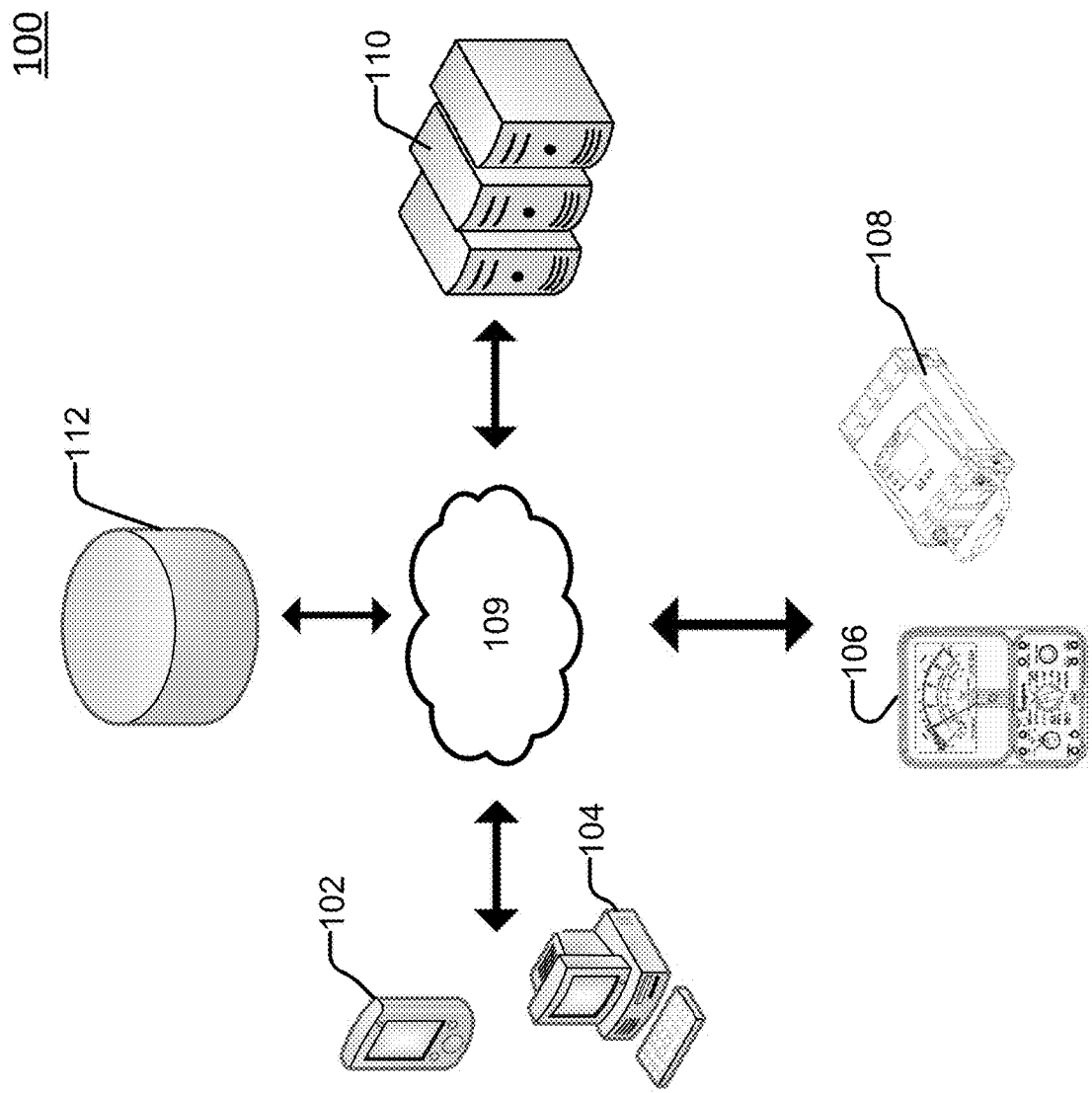
FIG. 1 is a system diagram of a system for CNG Methane number generation according to one example.

Aspects herein describe generation of a Methane number calculated using data obtained from a specific analyzer and according to a specified algorithmic protocol selected from a preset group of formulae as determined by both the specific analyzer and the selected compliance requirements. In some embodiments, the Methane number calculation formula is, more specifically, dictated by a) the particular chromatographic analyzer employed at the target facility (e.g., DANIELS, Asea Brown Boveri (ABB), SIEMENS®, YOKOGAWA®); b) according to the prevailing "local" standards (e.g., ISO (International Organization for Standardization), California, SAE, and other similar protocols), and/or c) specific Methane number generation requirements of an engine manufacturer (e.g., Caterpillar® for large mining vehicles, Cummins Westport® for over the road trucks, Wärtsilä® for marine engine applications) to maintain the validity of a vehicle engine warranty. The Methane number can then be used to refine CNG until it meets the designated Methane number.

The systems and methods described herein can be associated with the SOFTVIEW® software suite that is proprietary to Mustang® Sampling of Ravenswood, W. Va. However, the features are non-exclusive to combination with the SOFTVIEW® software suite and are subject to utilization in other embodiments. In one aspect, the SOFTVIEW® software suite can facilitate Methane number generation by interfacing both locally and remotely to a wide array of instrumentation using features such as an intuitive user interface, sub-routines, a station network user interface, instrument configuration, and history logging and trending. The SOFTVIEW® software, in particular, is a sub-routine within Cline SofTechnology (CST) Monitor/2000 SCADA (supervisory control and data acquisition) Gateway Executive software running on top of a Windows-based platform. The SCADA Gateway Executive (SGX) engine is the same engine which drives CST SCADA Systems.

The SOFTVIEW® suite includes SOFTVIEW® LITE, SOFTVIEW® LNG, SOFTVIEW® PLUS, and SOFTVIEW® PLUS+ configurations available for use with, but not limited to, Mustang® Sampling analyzers, vaporizers, chromatographs, and other equipment. The SGX engine for the SOFTVIEW® software suite includes at least four components such as instrument sub-routines defining an interface to each instrument, one or more sub-routine files having configuration settings for the sub-routines, data base files for the sub-routines, and unique code or logic for the sub-routines written in SGX application support language (ASL).

The systems described herein can be practiced in combination with software, such as SOFTVIEW®, that interfaces to other systems (e.g., distributed control system (DCS) or SCADA) which are configured to communicate with equipment used for collecting, recording, and reporting measurement data related to a custody transfer event (e.g., Mustang® Sampling vaporizers and associated gas chromatography instruments). In such embodiments, host systems such as DCS or SCADA acquire measurement data to facilitate management of data processing associated with custody. Preferably, the systems and methods described herein are capable of continuously collecting data from multiple sample conditioners and associated gas chromatographs.

Thus, methodologies described herein contemplate calculation of a particular Methane number from a matrix of Methane number measurement protocols and CNG measurement data obtained from select equipment. The matrix can be represented by a data table including a list of protocols along a first axis and a list of equipment/analyzers along a second axis, where each cell in the matrix/table represents a distinct result produced by pairing specific measurement equipment with a specific protocol.

It is further contemplated that generation of multiple Methane numbers may be achieved using a single gas composition value from an instrument, but calculated according to different Methane number protocols. Example Methane number calculations include protocols comprising ISO, Guobiao (GB), APA/ISO, APA/GB, and the International Group of Liquefied Natural Gas Importers (GIIGNL) defined standards, along with the average gas composition during custody transfer. Situations where multiple Methane numbers may need to be generated for a single gas supply include instances where a local regulatory protocol differs from the protocol required by the manufacturer of a particular CNG engine to maintain its warranty obligations.

As used herein, the singular forms, "a", "an", and "the" are intended to include the plural forms as well, unless the context clearly indicates otherwise. It will be further understood that the root terms "include" and/or "have", when used in this specification, specify the presence of stated features, steps, operations, elements, and/or components, but do not preclude the presence or addition of at least one other feature, step, operation, element, component, and/or groups thereof.

As used herein, the terms "comprises," "comprising," "includes," "including," "has," "having", or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus.

In the detailed description, references to "one embodiment", "an embodiment", or "in embodiments" mean that the feature being referred to is included in at least one embodiment of the invention. Moreover, separate references to "one embodiment", "an embodiment", or "embodiments" do not necessarily refer to the same embodiment; however, neither are such embodiments mutually exclusive, unless so stated, and except as will be readily apparent to those skilled in the art. Thus, the invention can include any variety of combinations and/or integrations of the embodiments described herein.

As used herein, and unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

In the following description, reference is made to the accompanying drawings, which is shown by way of illustration to a specific embodiment in which the invention may be practiced. The following illustrated embodiment is described in sufficient detail to enable those skilled in the art to practice the invention. It is to be understood that other embodiments may be utilized and that structural and methodological changes based on presently contemplated methods, known structures, and/or functional equivalents may be made without departing from the scope of the invention.

FIG. 1 is a system diagram of a system 100 for CNG Methane number generation according to one example. The system 100 includes one or more computers 104 and mobile devices 102 that can connect to one or more servers 110, databases 112 and equipment 106, 108 via network 109. The servers 110 are connected to one or more databases 112 and equipment 106, 108 either directly or through network 109. In one example, the one or more of the servers 110 have stored thereon code for executing the methods described herein thereby providing the overall functionality of the system 100. The servers 110 can perform the methods described herein using data stored internally or from the databases 112. The servers 110 also receive information from one or more pieces of external equipment 106, 108. For example, the system 100 can include chromatographic equipment 106 and a Micro-Motion (MM) Coriolis meter 108. These are examples of test equipment but it is contemplated that other types of text equipment can connect to the system 100. For example, additional equipment can include MHR and MV instruments for measuring temperature as well as vaporizer equipment for providing temperature input/output values such as inlet, outlet and gas. The external equipment 106, 108 is also known generally as analyzers and thus this term is used interchangeably herein.

Users can access the system 100 by using the computer 104 and/or mobile device 102. In one example, the computer 104 and/or mobile device 102 includes the software to perform the methods described herein. In this case, the computer 104 and/or mobile device 102 would receive information from the test equipment 106, 108, and additionally as needed, information from the servers 110 and databases 112 to perform the methods described herein. However, the computer 104 and/or mobile device 102 can also act as a front end for accessing performance data generated based on execution of the methods described herein by the one or more servers 110.

Figure 2:
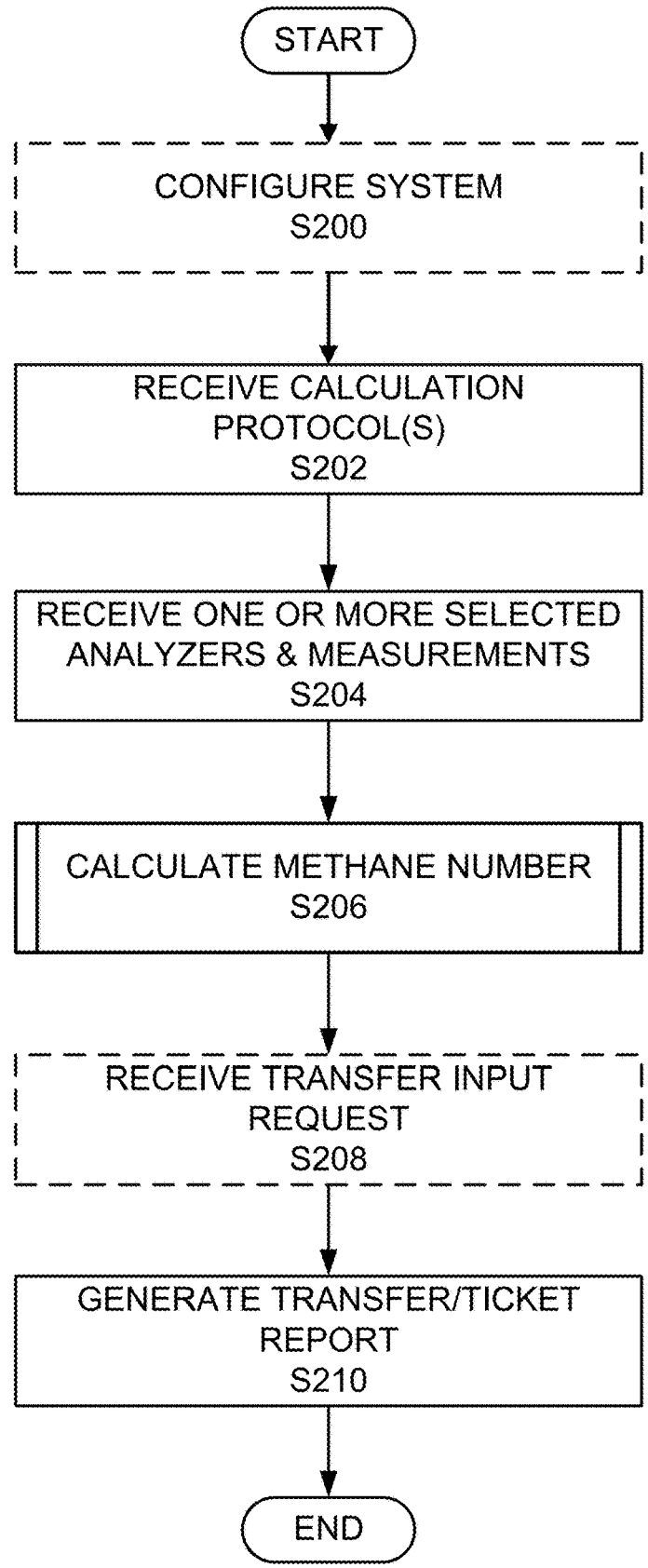
FIG. 2 is a flow chart diagram of a process for generating a report according to one example.

FIG. 2 illustrates a method of generating a transfer/ticket report using selectable analyzer(s) and selectable Methane number calculation protocols according to one example. It is noted that in one example, an optional preliminary step of configuring the system for field operation may be implemented at step 200. This can be accomplished by configuring defaults tables, defining vaporizer gas chromatograph configuration, defining/testing instrument communications interface, updating the station network for active vaporizer gas chromatographs, configuring the programming to configure the server 110 as a Modbus Transmission Control Protocol (TCP) Server for a DCS/SCADA ethernet interface, and/or configuring the programming to configure the server 110 as a Modbus Remote Terminal Unit (RTU) Server for a DCS/SCADA serial interface.

At step S202, calculation protocols providing various methods for calculating one or more Methane numbers are selected. The system database 112 stores a number of measurement criteria and predefined protocols used to produce information on the generated transfer ticket/report at step 210. For example, the generated Methane number(s) is calculated according to at least one of the following selected standardized protocols:

1) ISO Methane Number method;
 2) GB Methane Number method;
 3) APA/ISO Methane Number method;
 4) APA/GB Methane Number method.

It should be noted that steps 202-204 are not required to be in the order indicated above and could be performed in the opposite order. In one example, step 202 could be performed first at which point, once the server 110 receives one or more selected protocols, the server 110 will automatically readjust offered selections for the analyzers and types of measurements for step S204 based on the selected protocols. Alternatively, the selection of protocols at step S202 may be adjusted after the user selects one or more types of analyzers and/or measurements such that only protocols that are compatible with the particular analyzer are utilized by the system to calculate the Methane number. This facilities ease of use for the user and reduces the chance of errors in the Methane number calculation process.

In one exemplary embodiment, at step 204, the server 110 receives a selection of one or more analyzers and measurements from equipment 106, 108 and receives gas composition values based on gas composition measurements from the selected equipment (i.e. gas chromatograph) for use in the calculation of the Methane number at step 206. This selection can include options for identifying the type of equipment and the type of measurement desired for the particular protocol-based calculation. Accordingly, it may be desirable in particular applications of the selected protocols to involve further measurement data using instrumentation or criteria that augments the generated Methane number. Therefore, while the following measurements/criteria 5-18, supplement and enhance the generated Methane number determined at step 206 to provide useful information on the transfer ticket/report at step 210, particularly in custody transfer operations, they are not necessary for generating the Methane number. Accordingly, measurements may 5-18 be omitted. The additional measurements/criteria include:

1) Total BTUs;
 2) Total volume of liquefied natural gas (LNG) weight transferred;
 3) MM.LNG Density;
 4) MM.LNG Temperature;
 5) MM.LNG Mass F rate;
 6) MHR.TEMP;
 7) MV.TEMP;
 8) J4.LNG Temperature;
 9) J5.LNG Temperature;
 10) J9.LNG Inlet Temperature;
 11) J3.LNG Inlet Pressure;
 12) J7.LNG Vapor Gas Temperature;
 13) Inlet Solenoid Percent-Open; and
 14) Speed Loop Flow Percent.

In select examples, as would be understood by one of ordinary skill in the art, criteria 5 and 6 involve a weight measurement input; criteria 7 through 9 use input from an optional Micro-Motion Coriolis meter; criteria 10 and 11 include the temperature regulated by an optional Mustang Heated Regulator (MHR) or an optional Mustang Vaporizer (MV) instrument; and criteria 12 through 18 individually or collectively can use input from an optional Mustang Model 2 Vaporizer instrument.

Accordingly, in one example, at step 204, both the type of instrument and type of desired measurements may be selected and the gas composition measurements values are determined. Alternatively, the type of instrument may be selected at which point the server 110 automatically determines that appropriate types of measurements for the particular protocol-based calculation. Similarly, the types of measurements could be selected at which point the server 110 could automatically identify the type of instrument required for such a measurement.

Once steps 200-204 have been performed, the server 110 proceeds to calculate the Methane number at step 206. The way in which the server 110 calculates the Methane number is based on the selection of the calculation protocol in step 202. As such, the generation of Methane number(s) is performed by applying measured average gas composition values to the specifically selected Methane number calculation protocols. The calculation of the Methane number is further described with respect to FIG. 3.

Figure 3:
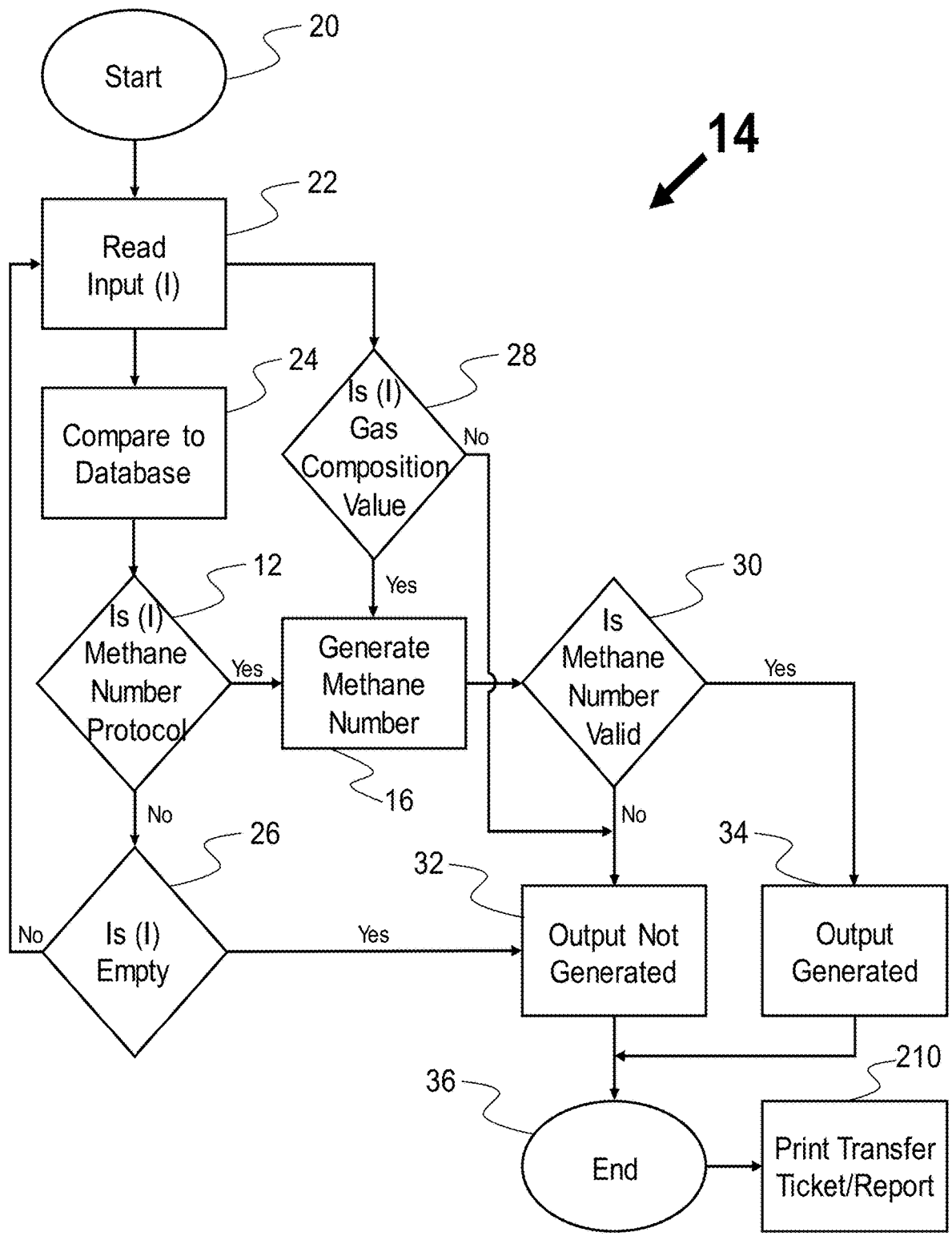
FIG. 3 is a flow chart diagram of calculating the Methane number according to one example.

FIG. 3 illustrates the process 14 for calculating a Methane number from preselected Methane number calculation protocols using the measured average gas composition during custody transfer according to one example. A start transfer action 20 is used to initiate the start of a custody transfer. This action 20 may be suspended, resumed, or ended as needed to facilitate optimal use.

Since the data fields for the analyzer(s) and the Methane number calculation protocol(s) are received prior to initiating the start transfer action 20, a read input function is performed by server 110 at step 22 to identify the selected information in each data field, which is individually compared at step 24 to a predefined list of Methane number calculation protocols stored in the database 112 and/or server 110. If at step 12 the data field matches the first protocol on the predefined list, the server 110 applies that protocol to generate a Methane number at step 16 using a gas composition value received from at least one analyzer at step 28. If the data field does not match the first protocol on the predefined list, steps 22 and 24 are repeated for each subsequent protocol in the predefined list until either a match is found or the list of Methane number calculation protocols is exhausted.

The process 14 is likewise configured to determine at step 26 whether a data field is empty following a "non-match". An empty input signals an "output not generated" operation at step 32. In cases where no output is generated, it is preferable that Methane number generation information corresponding to the empty data field remains absent from the printed transfer ticket/report.

Following exhaustion of the predefined list of Methane number calculation protocols, step 22 is once again performed to determine whether the input field has identified an analyzer for supplying an average gas composition value at step 28 through an instrument routine. If an average gas composition value has been supplied, the process 14 applies that value to "matched" Methane number calculation protocol(s) for generating Methane number(s) in accordance therewith. In certain aspects, a Methane number is generated at step 16 for up to all combinations of identified gas composition values and "matched"/selected Methane number calculation protocols.

In applying the obtained average gas composition value 28 to matched Methane number calculation protocol(s) 12, specific algorithms are selected in order to comply with different standards/requirements. Example approaches to Methane number calculations include the following list of formulas:

Motor Octane Number (equation 1):

$$MON = -406.14 + 508.04*(H/C) - 173.55*(H/C)^2 + 20.17*(H/C)^3$$

Where:

(H/C)=Total Hydrogen to Carbon Ratio

Methane Number Based on ISO—California Alt Fuels (equation 2):

$$MN\ ISO = 1.624*MON - 119.1$$

Where:

MON=value calculated from equation 1

Methane Number based on GB 18047-2000 (equation 3):

$$MN\ GB = 1.445 MON - 103.42$$

Where:

MON=value calculated from equation 1

APA Methane Number based on ISO (equations 4):

$$APA\ MN = A*MN\ ISO^3 + B*MN\ ISO^2 + C*MN\ ISO + D$$

Where:

$A = +1.01939E-03$ $B = -2.85817E-01$ $C = +2.75239E+01$ $D = -8.23574E-02$

MN ISO=Methane number calculated from equation 2

APA Methane Number based on GB (equation 5):

$$APA\ MN = A*MN\ GB^3 + B*MN\ GB^2 + C*MN\ GB + D$$

Where:

$A = +1.01939E-03$ $B = -2.85817E-01$ $C = +2.75239E+01$ $D = -8.23574E-02$

MN GB=Methane number calculated from equation 3 where A-D represent numerical constants.

In some instances, an average gas composition value 28 may not be found. This can occur when the start transfer action 20 is initiated without selecting an analyzer for providing the average gas composition value through an instrument routine. The result of such an action is to proceed to step 32 where no output is generated for the printed transfer ticket/report because no gas composition value was received at step 28 for generating the output at step 34.

Invalid gas composition values 28 include a value of "0", for example from a lack of communication with the analyzer, or flawed values derived from faulty measurement readings by the instrument itself. Thus, the process 14 performs a check at step 30 to determine whether the generated Methane number is a valid Methane number 30 by comparing it to an expected range of values. If the generated Methane number is not valid, the process 14 proceeds to step 32 where no output is generated. If the generated Methane number is valid, however, an output is generated at step 34 and produced on the transfer ticket/report at step 210 following an end of the process 14 at step 36.

Referring again to FIG. 2, once the Methane number has been calculated, the server 110 determines whether there are any received transfer inputs at step 208. This step is optional if the user desires to obtain additional information on the report generated at step S210. For example, a user may request information regarding the total MBTU (Million British Thermal Units) indicating the LNG BTUs transferred. A user could also request total volume indicating the LNG weight transferred.

Once step S208 is completed, the process proceeds to step 210 wherein an associated transfer ticket/report is generated including a generated Methane number calculated according to the requirements of individually selected criteria. Possible outcomes for the generated Methane number(s) include a matrix of Methane number values resulting from a particular protocol being selectively paired with a particular analyzer(s) which provides a measured gas composition. In one example, the matrix is represented by a set of protocols defining a first axis and a set of equipment/analyzers defining a second axis, where each cell in the matrix corresponds to a Methane number value generated according to the distinctly paired criteria. Multiple calculations according to differing Methane number generating protocols may be conducted coincidentally to provide different Methane numbers generated according to different protocols where the respective Methane numbers are required.

The transfer ticket/report also summarizes the average data collected from gas chromatograph and/or vaporizer information during the transfer. The transfer ticket/report may be printed as either a physical document or as an electronic document which can be stored and viewed for later reference. Optional measurement information, such as gas density, liquid density, total BTUs transferred in the load, etc., is included on the transfer ticket/report to supplement the information listed thereon. The transfer ticket/report further includes a ticket header with information that is optionally edited (e.g., carrier, carrier type, dock ID, tank ID, inspector name, etc.) for a particular transfer ticket.

Figure 4:
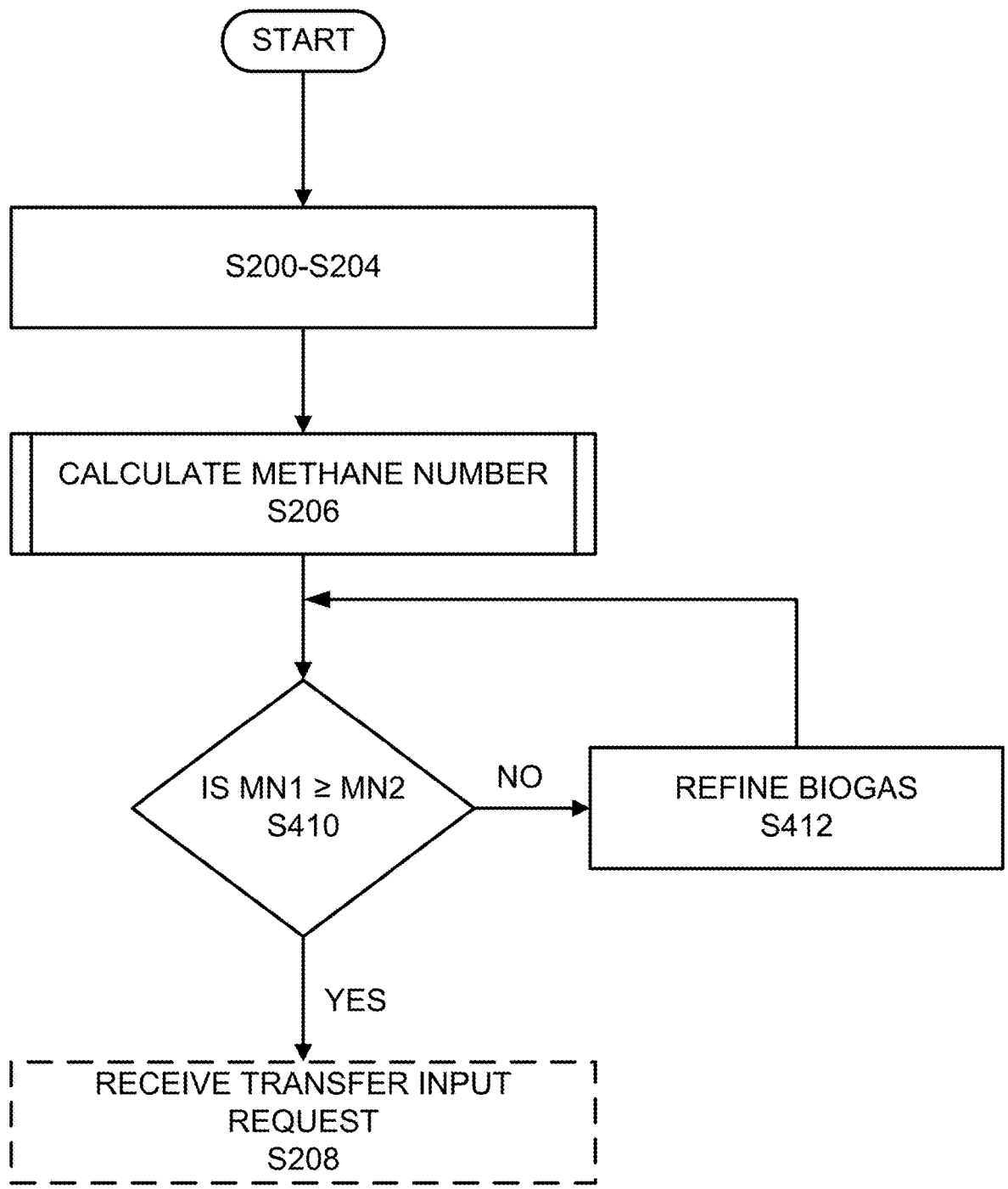
FIG. 4 illustrates a flow chart diagram of adjusting a biogas based on the Methane number according to one example.

FIG. 4 represents a process for adjusting a gas stream from a selected source, in this case a biogas, exhibiting a calculated methane number that falls outside a permitted threshold by blending the biogas with a purified gas from a select source to obtain a blended gas possessing a Methane number in a select desired range. The feedback control process is an optional additional process to the processes described in FIG. 2. For such a feedback control process, steps 200-206 are the same as those described above to achieve compliance with respect to the Methane number. For the purposes of this example, the selected standard Methane number is designated as MN2 and the actual calculated Methane number is MN1. Once the calculated Methane number MN1 is established, it is compared to the Methane number of a selected compliance standard MN2. If the calculated Methane number MN1 is greater than or equal to the selected compliance standard MN2, then the process permits release of the biogas and generates a report at step 210 as previously described herein. If, however the calculated Methane number MN1 falls outside the selected compliance standard, the server 110 generates a signal to a gas blending control station to inject into and blend a refined gas possessing a known Methane Number with the gas from the select source at step 412. Until the resulting blended gas stream possesses a satisfactory Methane Number, the process may be repeated in a looped process until the calculated Methane number MN1 is greater than or equal to the selected compliance standard MN2. For example, methane can be introduced into the stream to increase the calculated Methane number MN1. Alternatively, if it is desired for the Methane number value of MN1 to be lowered to meet a standard Methane number MN2, ethane could be injected into the stream to lower the calculated Methane number MN1 and the loop could be repeated until the calculated Methane number MN1 is less than or equal to the selected standard MN2.

The gas blending system, as described, provides a biogas energy content and blending system adapted for monitoring characteristics of a biogas feedstock stream from a first source and for controlling introduction of a refined gas from a refined gas source, such as natural gas or propane with a known, elevated energy content value, to yield a blended biogas satisfying the requirements of specific standards and/or established CNG engine warranty protocols. Accordingly, exemplary descriptions provided herein describe how the energy content of the biogas can be refined which in turn adjusts the Methane number based on continuous calculations corresponding to specified protocols.

A combined Methane Number generator system as described above is readily combinable with a gas blending system that is readily employable in combination with a multi-stage system providing a biogas feedstock stream as described in patent U.S. Pat. No. 9,535,045, the entirety of which is herein incorporated by reference. The refined gas stream, possessing a combustion energy profile suitable for increasing the overall energy content of the biogas feedstock stream, is selectively introduced into the biogas feedstock stream.

In one example, the gas blending system includes at least a first and second sample takeoff probe disposed in the biogas feedstock and blended biogas streams at positions before and after the gas blending pipe section, respectively. The first sample takeoff probe is used to extract an unblended sample from the biogas feedstock stream, which is directly communicated to an appropriate analyzer, e.g., a gas chromatograph (GC). When the combustion energy level of the unblended biogas is detected as falling below a preselected minimum, a signal from a control unit is transmitted to open an actuatable valve (e.g., electro-mechanical, solenoid valve, etc.) disposed between the refined gas source and the biogas feedstock stream. Upon actuation, the valve switches from a closed to a modulated open or fully open position to introduce refined gas into the biogas feedstock stream to create a blended biogas with a higher overall energy content. The second sample takeoff probe located downstream extracts a sample of blended biogas downstream from the refined gas injection which is passed to an analyzer for compositional/energy content evaluation. Data obtained from the blended biogas sample is transmitted from the analyzer to a control unit for verification of achieving the necessary enhancement of the energy content to satisfy the quality requirements of the end-user. The data also is employed to control the flow rate of the refined gas injected into the biogas feedstock stream to minimize waste resulting from introducing excessive refined gas into the biogas feedstock stream.

Introduction of the refined gas into the biogas feedstock stream is not necessarily continuous. When the compositional/energy content of the unblended biogas feedstock sample from the first take-off is determined to be sufficient, there is no need to augment the energy profile of the biogas feedstock steam. In such a case, the control unit maintains the actuatable valve in the closed position and allows the biogas feedstock stream to pass to the system output without refined gas blending.

The inventive gas blending method and system may also incorporate flow sensors for detecting and measuring the flow of the unblended biogas feedstock stream and the flow of the refined gas stream providing signal transmission to a control unit. The resulting flow rate determinations provide additional data to supplement determinations of energy content analysis of the respective biogas stream and refined gas input. Such flow rate measurements may provide enhanced accuracy as a redundant alternative measurement confirming that a proper blend has been obtained and may signal the need to increase or decrease the quantity of refined gas being injected into the biogas feedstock stream. If the processed flow rate data a need to increase or reduce refined gas flow volume, the control unit sends a signal indicating the need to modulate refined gas flow through the valve.

The inventive gas blending method and system may also incorporate a refined gas impingement tube adjunct at the point of injection to promote more uniform cross-sectional introduction of the refined gas into the biogas feedstock stream.

Once the energy content of the gas has been refined at step S412 such that the calculated Methane number MN1 is greater than or equal to the selected compliance standard MN2, the process proceeds to step S208 where a user can optionally submit a transfer input request as previously described herein. A report will then be generated at step S210 as previously described herein. In this case, the report will include additional information, such as the audit documents, with respect to refinement via the gas blending system control station.

Figure 5:
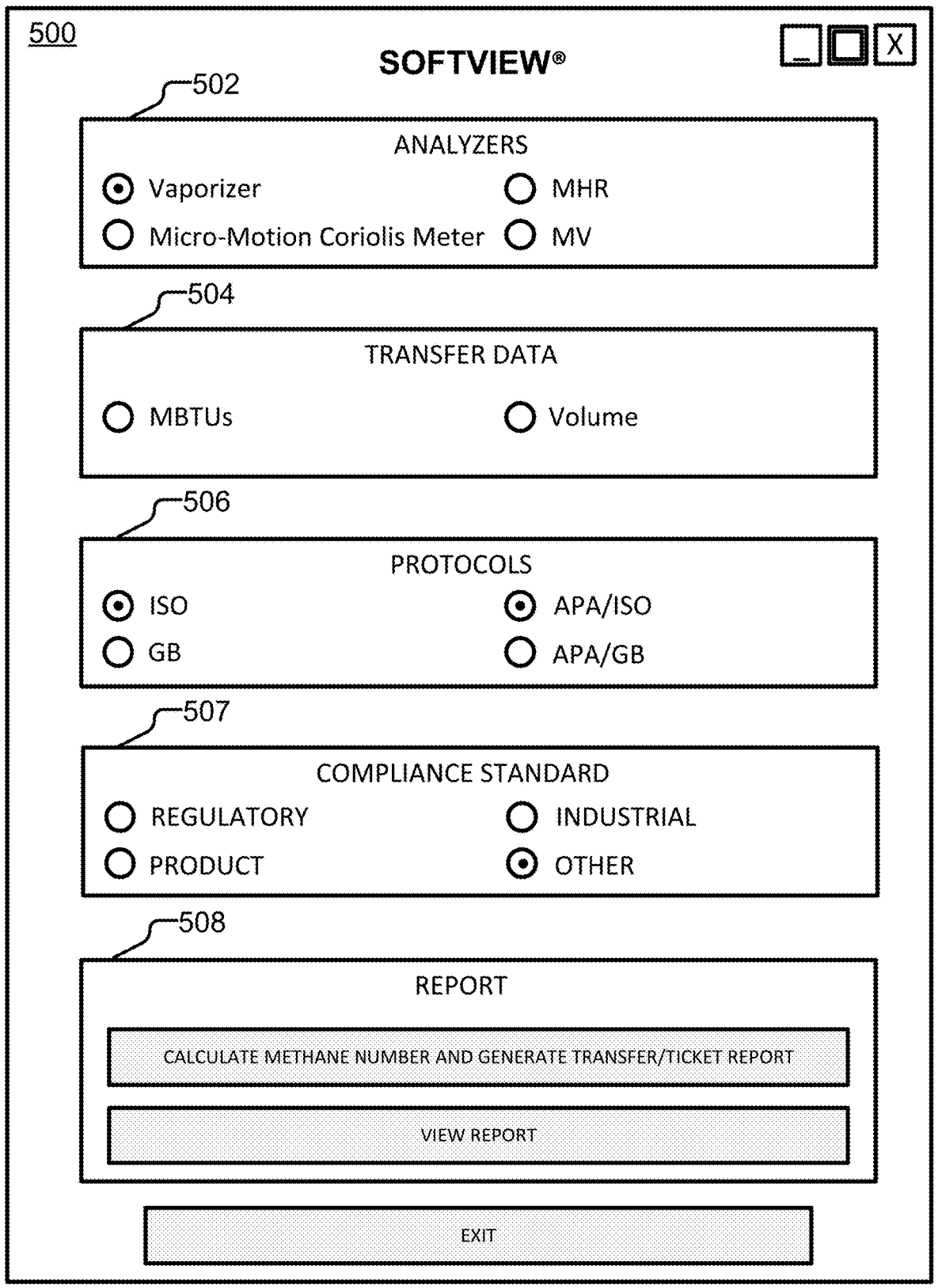
FIG. 5 illustrates a user interface for generating a methane number and associated transfer ticket report according to one example.

FIG. 5 illustrates a user interface 500 for generating a Methane number and associated transfer ticket according to one example. The user interface 500 includes a plurality of windows 502-708 for configuring and performing the processes described herein. In window 502, the user interface 500 receives selections for the types of analyzers that are used in the Methane number calculation process. As illustrated in FIG. 5, one or more analyzers can be selected by clicking on the associated radio buttons. In this example, the vaporizer has been selected as an analyzer to enhance the calculation of the Methane number.

Window 504 allows for the selection of transfer data such as the LNG MBTUs and the LNG volume so that this data can be included in the report. In this example, no radio button is selected and therefore neither of these items will be included in the report.

Window 506 provides for the selection of one or more protocols to be used to calculate the Methane number. As show in the illustrative example of FIG. 5, two protocols have been selected (e.g., ISO, APA/ISO) such that the system will provide two different Methane numbers based on the respective calculations. Once the protocols have been selected in window 506, the Methane number can be calculated by hitting the button in window 508. This will also create the transfer/ticket report to be stored locally on server 110, computer 104 and/or database 112. A user can also review the report by clicking on the review report button included in window 508. Once the user is finished, the user may exit by hitting the exit button. In the context of the process of FIG. 4, the calculate Methane number and generate transfer/ticket report and view report buttons of window 508 can provide real-time information regarding the continuous blending of biogas to achieve a Methane number of a predetermined amount and/or an after-blending audit report. Accordingly, the report will show a history of values from an initial Methane number to a final methane number along with corresponding equipment values, Methane number values and protocol values.

In one example, the user interface 500 may be configured such that the buttons of window 508 are greyed out and not selectable until at least one protocol has been selected. Further, window 502 may be configured such that selectable options therein are greyed out until a protocol has been selected in window 506. Once the protocol has been selected, the user interface will be refreshed such that window 502 only allow options to be selected which correspond to the selected protocol. This reduces user error and makes the operation of the system easier to determine Methane numbers.

If the user is attempting to refine the gas to achieve a selected compliance standard, the user can select a particular standard such as regulatory, product or industrial. A list of regulatory selections can be provided such as compliance standards by locale. Further, a list of industrial standards, such as automotive, can also be provided. In addition, product standards, such as for particular product engines, can also be provided. Further, a user can select other to identify a particular Methane number MN2 for comparison to the calculated Methane number MN1.

Additional interfaces are also contemplated and encompassed by the description herein. For example, a load summary station window and a load action button can be included on the station network to initiate a custody transfer procedure. The process 14 provides popup messages in response to actions in order to denote action processing. A configuration window also provides the ability to enter information such as arrival, docked, and connected dates/times for the transfer ticket. In select examples, such as those comprising SOFTVIEW®, instrument routines like "011 Vaporizer Instruments APP", "012 Daniel GC Instruments APP", and "013 ABB NGC Instruments APP" incorporate data received from associated instruments. Other routines such as "001 Vaporizer GC Data Reports APP", "002 GC Comp Reports APP", "007 Vaporizer Configurations APP", "025 LNG Production Reports APP", and "026 Mustang LNG APP" are non-instrument routines used for processing 14 and configuration.

In one example, a configuration window (not shown) can be accessed to revise the transfer ticket/report (e.g., to filter data or enter disconnect and depart dates/times). Certain routines permit data averages to be filtered from the transfer ticket/report based on periods of time when the transfer should have otherwise been suspended. Two available filtering methods include filtering specific records by record number and filtering BTU values outside of a defined range. Once the desired final transfer ticket is obtained, the ticket may be archived via an archive load action and stored for later viewing, as needed.

Figure 6:
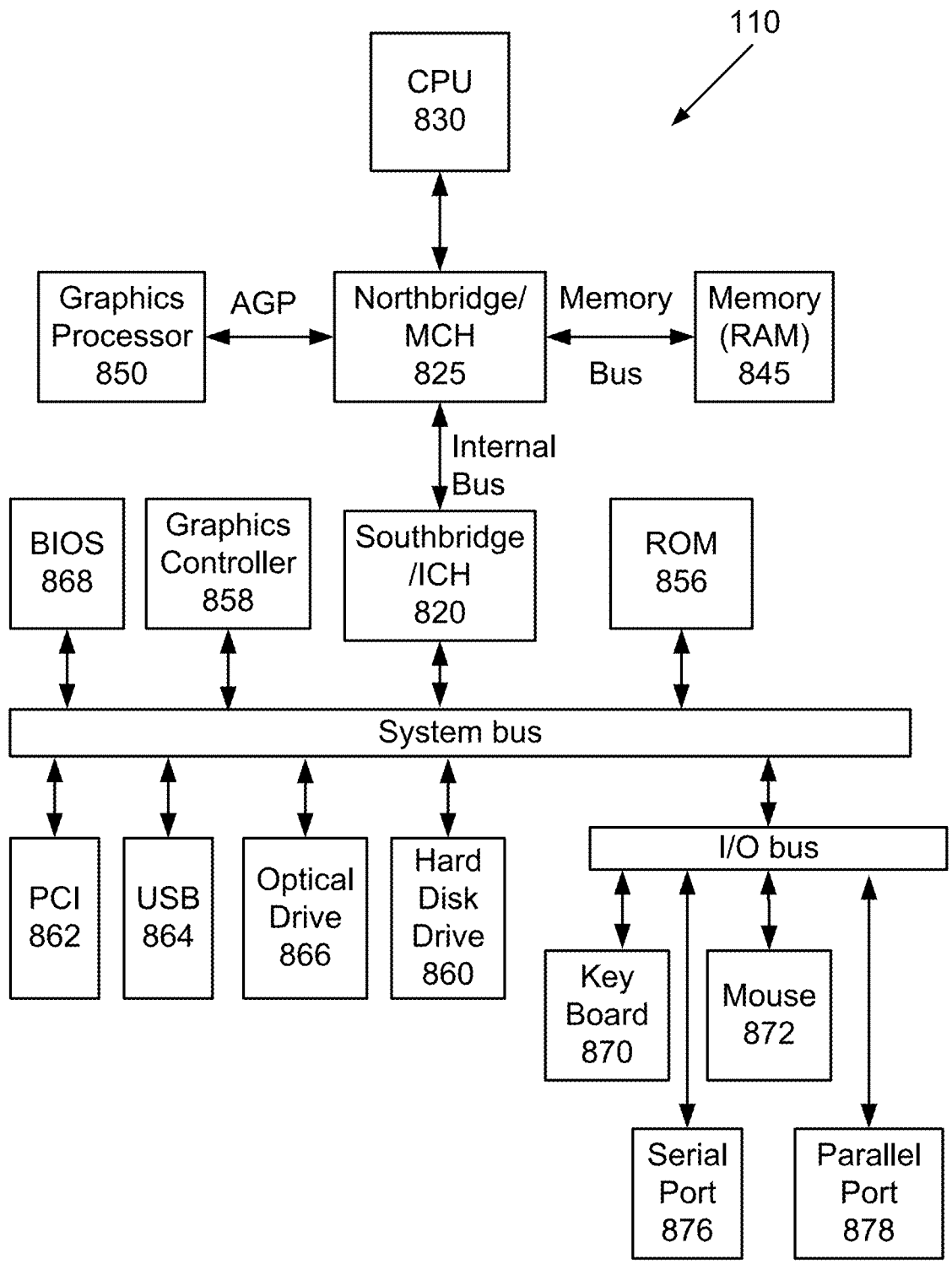
FIG. 6 is a schematic diagram of a server, according to one example.

FIG. 6 shows a schematic diagram of the server 110, according to certain examples, for performing the processes described herein. The server 110 is an example of a computer in which code or instructions implementing the processes of the illustrative embodiments may be located.

In FIG. 6, server 110 employs a hub architecture including a north bridge and memory controller hub (NB/MCH) 825 and a south bridge and input/output (I/O) controller hub (SB/ICH) 820. The central processing unit (CPU) 830 is connected to NB/MCH 825. The NB/MCH 825 also connects to the memory 845 via a memory bus, and connects to the graphics processor 850 via an accelerated graphics port (AGP). The NB/MCH 825 also connects to the SB/ICH 820 via an internal bus (e.g., a unified media interface or a direct media interface). The CPU Processing unit 830 may contain one or more processors and even may be implemented using one or more heterogeneous processor systems.

Figure 7:
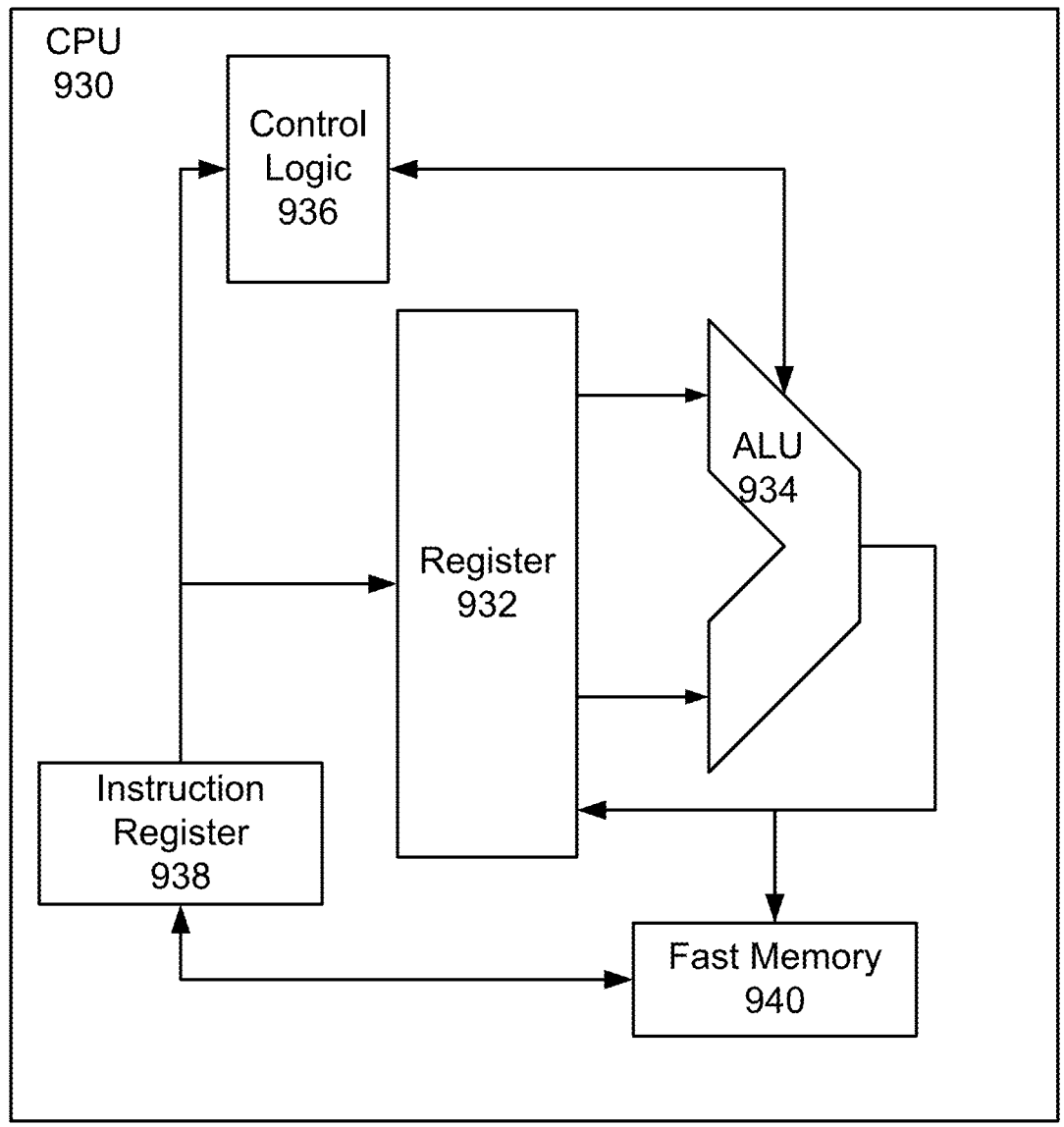
FIG. 7 illustrates a central processing unit (CPU) of the server according to one example.

For example, FIG. 7 shows one exemplary implementation of CPU 830. In one implementation, the instruction register 938 retrieves instructions from the fast memory 940. At least part of these instructions are fetched from the instruction register 938 by the control logic 936 and interpreted according to the instruction set architecture of the CPU 830. Part of the instructions can also be directed to the register 932. In one implementation the instructions are decoded according to a hardwired method, and in another implementation the instructions are decoded according a microprogram that translates instructions into sets of CPU configuration signals that are applied sequentially over multiple clock pulses. After fetching and decoding the instructions, the instructions are executed using the arithmetic logic unit (ALU) 934 that loads values from the register 932 and performs logical and mathematical operations on the loaded values according to the instructions. The results from these operations can be feedback into the register and/or stored in the fast memory 940. According to certain implementations, the instruction set architecture of the CPU 830 can use a reduced instruction set architecture, a complex instruction set architecture, a vector processor architecture, a very large instruction word architecture. Furthermore, the CPU 830 can be based on the Von Neuman model or the Harvard model. The CPU 830 can be a digital signal processor, an FPGA, an ASIC, a PLA, a PLD, or a CPLD. Further, the CPU 830 can be an x86 processor by Intel or by AMD; an ARM processor, a Power architecture processor by, e.g., IBM; a SPARC architecture processor by Sun Microsystems or by Oracle; or other known CPU architecture.

Referring again to FIG. 6, the server 110 can include the SB/ICH 820 coupled through a system bus to an I/O Bus, a read only memory (ROM) Y56, universal serial bus (USB) port 864, a flash binary input/output system (BIOS) 868, and a graphics controller 858. PCI/PCIe devices can also be coupled to SB/ICH YYY through a PCI bus 862.

The PCI devices may include, for example, Ethernet adapters, add-in cards, and PC cards for notebook computers. The Hard disk drive 860 and CD-ROM 866 can use, for example, an integrated drive electronics (IDE) or serial advanced technology attachment (SATA) interface. In one implementation the I/O bus can include a super I/O (SIO) device.

Further, the hard disk drive (HDD) 860 and optical drive 866 can also be coupled to the SB/ICH 820 through a system bus. In one implementation, a keyboard 870, a mouse 872, a parallel port 878, and a serial port 876 can be connected to the system bust through the I/O bus. Other peripherals and devices that can be connected to the SB/ICH 820 using a mass storage controller such as SATA or PATA, an Ethernet port, an ISA bus, a LPC bridge, SMBus, a DMA controller, and an Audio Codec.

The functions and features described herein may also be executed by various distributed components of a system. For example, one or more processors may execute these system functions, wherein the processors are distributed across multiple components communicating in a network. The distributed components may include one or more client and server machines, which may share processing, as shown on FIG. 6, in addition to various human interface and communication devices (e.g., display monitors, smart phones, tablets, personal digital assistants (PDAs)). The network may be a private network, such as a LAN or WAN, or may be a public network, such as the Internet. Input to the system may be received via direct user input and received remotely either in real-time or as a batch process. Additionally, some implementations may be performed on modules or hardware not identical to those described. Accordingly, other implementations are within the scope that may be claimed.

Figure 8:
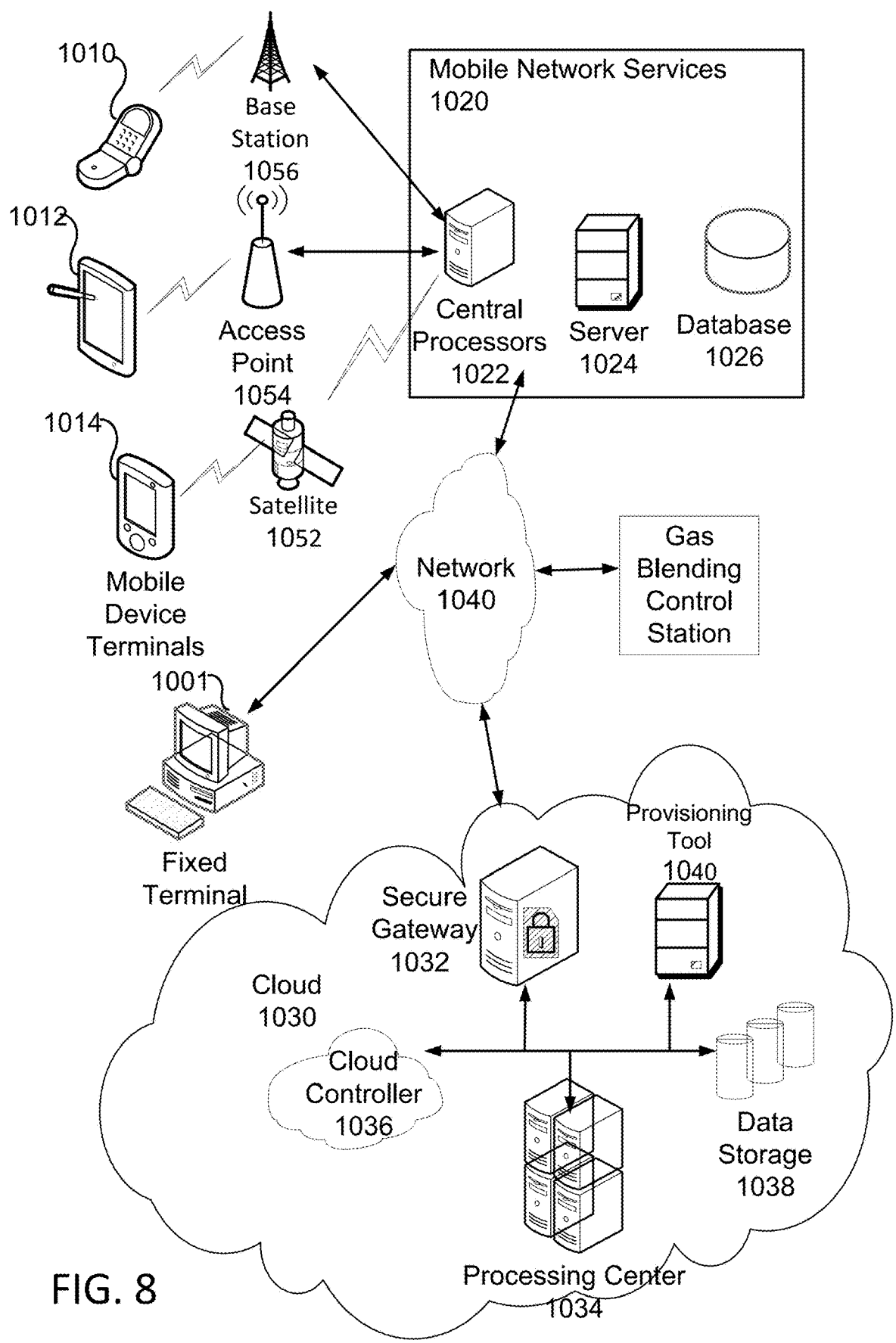
FIG. 8 illustrates a distributed cloud system according to one example.

FIG. 8 shows an example of cloud computing, having various devices interconnected to each other via a network and cloud infrastructures. Similarly, FIG. 6 shows a PDS 1012 and a cellular phone 1014 connected to the mobile network service 1020 through a wireless access point 1054, such as a femto cell or Wi-Fi network. Further, FIG. 8 shows a computer 1001, such as computer 104, connected to the mobile network service 1020 through a wireless channel using a base station 1056, such as an Edge, 3G, 4G, or LTE Network, for example. FIG. 8 also illustrates the connection of the gas blending control station via network 1040. Various other permutations of communications between the types of devices and the mobile network service 1020 are also possible, as would be understood to one of ordinary skill in the art. The various types of devices, such as the cellular phone 1014, tablet computer 1016, or a desktop computer, can also access the network 1040 and the cloud 1030 through a fixed/wired connection, such as through a USB connection to a desktop or laptop computer or workstation that is connected to the network 1040 via a network controller, such as an Intel Ethernet PRO network interface card from Intel Corporation of America, for interfacing with a network.

Signals from the wireless interfaces (e.g., the base station 1056, the wireless access point 1054, and the satellite connection 1052) are transmitted to and from the mobile network service 1020, such as an EnodeB and radio network controller, UMTS, or HSDPA/HSUPA. Requests from mobile users and their corresponding information as well as information being sent to users is transmitted to central processors 1022 that are connected to servers 1024 providing mobile network services, for example. Further, mobile network operators can provide services to the various types of devices. For example, these services can include authentication, authorization, and accounting based on home agent and subscribers' data stored in databases 1026, for example. The subscribers' requests can be delivered to the cloud 1030 through a network 1040.

As can be appreciated, the network 1040 can be a public network, such as the Internet, or a private network such as an LAN or WAN network, or any combination thereof and can also include PSTN or ISDN sub-networks. The network 1040 can also be a wired network, such as an Ethernet network, or can be a wireless network such as a cellular network including EDGE, 3G and 4G wireless cellular systems. The wireless network can also be Wi-Fi, Bluetooth, or any other wireless form of a communication that is known.

The various types of devices can each connect via the network 1040 to the cloud 1030, receive inputs from the cloud 1030 and transmit data to the cloud 1030. In the cloud 1030, a cloud controller 1036 processes a request to provide users with corresponding cloud services. These cloud services are provided using concepts of utility computing, virtualization, and service-oriented architecture. Data from the cloud 1030 can be accessed by the computer 1001 based on user interaction and pushed to user devices 1010, 1012, and 1014.

The cloud 1030 can be accessed via a user interface such as a secure gateway 1032. The secure gateway 1032 can, for example, provide security policy enforcement points placed between cloud service consumers and cloud service providers to interject enterprise security policies as the cloud-based resources are accessed. Further, the secure gateway 1032 can consolidate multiple types of security policy enforcement, including, for example, authentication, single sign-on, authorization, security token mapping, encryption, tokenization, logging, alerting, and API control. The cloud 1030 can provide, to users, computational resources using a system of virtualization, wherein processing and memory requirements can be dynamically allocated and dispersed among a combination of processors and memories such that the provisioning of computational resources is hidden from the users and making the provisioning appear seamless as though performed on a single machine. Thus, a virtual machine is created that dynamically allocates resources and is therefore more efficient at utilizing available resources. A system of virtualization using virtual machines creates an appearance of using a single seamless computer even though multiple computational resources and memories can be utilized according increases or decreases in demand. The virtual machines can be achieved using a provisioning tool 1040 that prepares and equips the cloud-based resources such as a processing center 1034 and data storage 1038 to provide services to the users of the cloud 1030, such as those described above with respect to server 110. The processing center 1034 can be a computer cluster, a data center, a main frame computer, or a server farm. The processing center 1034 and data storage 1038 can also be collocated.

In most instances, it is desirable for CNG suppliers and outlets to be able to adjust and/or manage supplies that comprise a Methane number. Accordingly, the systems and methods described herein provide selective monitoring and reporting of critical constituent contents needed to meet regulatory and/or quality specifications for CNG custody transfer and particularly in the context of CNG engine fueling. Accordingly, the systems and methods described herein provide the advantageous features of generating a Methane number produced according to the regional/local regulatory protocols and/or the monitoring requirements for compliance with engine operations from selectable criteria applicable to a variety of specific conditions. This prevents the issues previously discussed regarding engine knocking and an avoid the degradation of equipment which is an issue that has plagued the industry in costs and delays.

Further, the systems and methods described herein provide a technical solution to the technical problem of generating more accurate Methane numbers as well as refining gas to achieve the more accurate Methane numbers. The use of specific equipment and specific measurements to obtain real-time composition gas values for use in the protocol calculations enhances the accuracy of the Methane number calculation. This allows the user to fully comply with compliance standards in an industry in which requirements are constantly changing. It also allows the user to satisfy engine manufacturer warranty requirements for Methane number generation for motor vehicle fuel. Further, the ability to effectively and efficiently generate multiple Methane numbers based on varying protocols improves the technical field by no longer requiring various equipment to be recalibrated every time a different protocol measurement is required.

The accuracy of the Methane number is becoming increasingly important as it has been forecasted in the U.S. that natural gas as a fuel for transportation will grow at an annual average rate of 11.9% from 2011 to 2040. Further, having an enhanced accuracy of the Methane number will reduce engine knocking thereby improving the technical fields of fuel knock resistance composition and engine build and reliability. This is important when refining gas to adjust the Methane number as an accurate Methane number will reduce knockback incidents while also ensuring compliance with increasingly strict standards. This allows gas producers with non-compliant CNG motor vehicle fuel gas more flexibility in cleaning up their gas. For example, a gas producer with a high ethane content gas could chose to remove a portion of the heavier hydrocarbons to meet the proposed methane number specification rather than reducing the ethane, which is more difficult to remove. Additionally, these heavier hydrocarbons are more marketable, for example, in California than Ethane. Further, the blending is useful to meet tariffs when performing custody transfer between different areas, such as pipelines, and therefore having an accurate Methane number is crucial to enable effective and accurate custody transfer.

Accordingly, described herein is a system which makes use of a particular algorithm and is therefore not an abstract idea. Further, the systems and processes described herein recite significantly more than any abstract idea as they describe features which are not well-understood, routine or conventional and which also improve the technical field.

It is understood that the invention is not limited to the specific embodiments disclosed herein, and that many modifications and other embodiments of the invention are intended to be included within the scope of the invention. Moreover, although specific terms are employed herein, they are used only in a generic and descriptive sense, and not for the purposes of limiting the description of the invention.

What is claimed is:

1. A method comprising:
   monitoring during transfer of a compressed natural gas composition, via a first analyzing device configured to measure only a non-liquid compressed natural gas composition;
   receiving data from the first analyzing device, the data being representative of a compressed natural gas sample analysis during transfer;
   determining an average compressed natural gas composition as a function of data received over a period of transfer;
   determining at least a first set and a second set of established processes for Methane number generation compatible with the first analyzing device;
   selecting the at least first set of established processes corresponding to a first selected Methane number generation protocol;
   selecting the at least second set of established processes corresponding to a second selected Methane number generation protocol;
   applying, via at least one processor, at least said first and said second established processes to the average compressed natural gas composition to calculate at least a first Methane number as a function of the first selected Methane number generation protocol and a second Methane number as a function of the second selected Methane number generation protocol;
   comparing the first Methane number and second Methane number to respective predetermined thresholds; and
   adjusting a compressed natural gas composition to meet the respective predetermined thresholds.

2. The method of claim 1, wherein the first analyzing device includes one of a chromatograph, a Coriolis meter and a vaporizer.

3. The method of claim 1, further comprising:
   determining a set of established processes for Methane number generation compatible with a second analyzing device different from the first analyzing device;

selecting a third established process from the process set corresponding to a third selected Methane number generation protocol;

applying the third established process to the received data from the second analyzing device to calculate a third Methane number corresponding to the third selected Methane number generation protocol.

4. The method of claim 1, further comprising:

generating a transfer ticket report including the first Methane number and the second Methane number generated from the data received from the analyzing device.

5. The method of claim 1, further comprising:

performing configuration steps before processing the data obtained by the first analyzing device.

6. The method of claim 1, wherein the adjusting injects a refined gas having a known Methane number into the compressed natural gas composition.

7. A system comprising:

an analyzing device configured to measure only a non-liquid compressed natural gas composition sample obtained during transfer from compressed natural gas fuel to generate gas constituent data representative thereof; and processing circuitry in communication with the analyzing device, said processing circuitry configured to determine an average compressed natural gas fuel composition as a function of gas constituent data received during transfer, select a set of at least a first and a second established processes for Methane number generation compatible with the analyzing device, receive the at least first established process to generate a first Methane number, the at least second established process to generate a second Methane number, apply the at least first established process to the average compressed natural gas fuel composition to calculate a first Methane number, apply the at least second established process to the average compressed natural gas fuel composition to calculate a second Methane number, compare the first Methane number and the second Methane number to respective predetermined thresholds, and control a gas blending control station to adjust a compressed natural gas fuel as a function of the comparison.

8. The system according to claim 7, wherein the Methane number generation protocol is based on a type of industrial product.

9. The system according to claim 7, wherein the processing circuitry causes the gas blending control station to adjust the compressed natural gas fuel when the first Methane number and the second Methane number is less than the respective predetermined thresholds.

10. The system according to claim 7, wherein the gas blending control station adjusts the compressed natural gas fuel by injecting a refined gas having a known Methane number into the compressed natural gas fuel.

11. The system according to claim 7, wherein the analyzing device is one of a gas chromatograph and vaporizer.

12. The system according to claim 11, wherein the analyzing device is the gas chromatograph.

* * * * *